US012698535B1

(12) United States Patent
Gu et al.

(10) Patent No.: US 12,698,535 B1
(45) Date of Patent: Aug. 4, 2026

(54) MULTI-CANCER DETECTION AND TRACEABILITY SYSTEMS BASED ON DNA HIGH-THROUGHPUT METHYLATION SEQUENCING

(71) Applicant: HANGZHOU SHENGTING MEDICAL TECHNOLOGY CO., LTD, Hangzhou (CN)

(72) Inventors: Hongcang Gu, Hangzhou (CN); Yunfei Wang, Hangzhou (CN); Jian Huang, Hangzhou (CN); Qian Wang, Hangzhou (CN)

(73) Assignee: HANGZHOU SHENGTING MEDICAL TEHCNOLOGY CO., LTD, Hangzhou (CN)

( * ) Notice: Subject to any disclaimer, the term of this patent is extended or adjusted under 35 U.S.C. 154(b) by 0 days.

(21) Appl. No.: 19/259,024

(22) Filed: Jul. 3, 2025

(51) Int. Cl.
| | |
|---|---|
| *C12Q 1/68* | (2018.01) |
| *C12Q 1/6806* | (2018.01) |
| *C12Q 1/6869* | (2018.01) |
| *C12Q 1/6886* | (2018.01) |
| *G16B 30/00* | (2019.01) |
| *G16B 40/00* | (2019.01) |

(52) U.S. Cl.
CPC ......... *C12Q 1/6886* (2013.01); *C12Q 1/6806* (2013.01); *C12Q 1/6869* (2013.01); *G16B 30/00* (2019.02); *G16B 40/00* (2019.02); *C12Q 2600/154* (2013.01)

(58) Field of Classification Search
None
See application file for complete search history.

(56) References Cited

U.S. PATENT DOCUMENTS 12,227,737 B2 * 2/2025 Diniz De Carvalho .................... C12Q 1/6804

FOREIGN PATENT DOCUMENTS

WO WO-2024020036 A1 * 1/2024 ............. G16B 20/00

OTHER PUBLICATIONS

Hong et al. (Nucleic Acids Research, 2024, 52: D929-937, earliest publication date of Oct. 13, 2023) (Year: 2024).*
Xu et al. (Nature Communications, 2021, 12:400, p. 1-9) (Year: 2021).*
Li et al. (Nucleic Acids Research, 2018, 46 (15):e89, p. 1-11) (Year: 2018).*
Gao et al. (Annals of Oncology, 2023, 34(5): 486-495) (Year: 2023).*

* cited by examiner

*Primary Examiner* — Stephanie K Mummert
(74) *Attorney, Agent, or Firm* — Cooper Legal Group, LLC

(57) ABSTRACT

Provided are multi-cancer detection and traceability systems based on DNA high-throughput methylation sequencing. The multi-cancer detection system includes a first sample sequencing module used for sequencing sample DNA, a methylation feature set acquisition module used for comparing methylation levels of sequencing data to obtain a methylation feature set, a terminal motif feature acquisition module used for counting proportions of terminal motif base fragments in all permutations and combinations to obtain a terminal motif feature, a breakpoint motif feature acquisition module used for counting proportions of breakpoint motif base fragments in all permutations and combinations to obtain a breakpoint motif feature, and a model building module used for training a learning classification module by taking the methylation feature set, the terminal motif feature and the breakpoint motif feature as input and whether cancer is suffered from and a probability of the cancer as output to obtain detection and traceability models.

9 Claims, 12 Drawing Sheets

| | Healthy person n=436 | Lung cancer n=190 | Colorectal cancer n=291 | Gastric cancer n=47 | Liver cancer n=65 | Thyroid cancer n=146 | Breast cancer n=46 |
|---|---|---|---|---|---|---|---|
| Healthy person n=489 | 420 | 35 | 8 | 3 | 4 | 17 | 2 |
| Lung cancer n=191 | 11 | 108 | 14 | 6 | 11 | 31 | 10 |
| Colorectal cancer n=308 | 3 | 21 | 259 | 10 | 6 | 8 | 1 |
| Gastric cancer n=40 | 1 | 4 | 4 | 28 | 0 | 2 | 1 |
| Liver cancer n=44 | 0 | 0 | 0 | 0 | 44 | 0 | 0 |
| Thyroid cancer n=101 | 1 | 9 | 3 | 0 | 0 | 85 | 3 |
| Breast cancer n=48 | 0 | 13 | 3 | 0 | 0 | 3 | 29 |

Predicted value

True value

MULTI-CANCER DETECTION AND TRACEABILITY SYSTEMS BASED ON DNA HIGH-THROUGHPUT METHYLATION SEQUENCING

TECHNICAL FIELD

The present application relates to the technical field of molecular biomedicine, and particularly to multi-cancer detection and traceability systems based on DNA high-throughput methylation sequencing.

BACKGROUND ART

Malignant tumors are a kind of diseases that seriously threaten human health. At present, the average 5-year survival rate for patients with malignant tumors is approximately 35%. Although the survival rate has been improved in recent years, there is still considerable room for improvement. This is mainly because the early screening and diagnosis rate of the malignant tumors is low, causing that most patients are at an advanced stage when diagnosed and have a poor prognosis. In addition, the treatment cost for early-stage tumors is significantly lower than that for advanced-stage tumors. Therefore, screening and diagnosis of the early-stage tumors can not only significantly improve the survival rate of the patients, but also greatly reduce the medical expenditure burden of countries and individuals. In particular, the pan-cancer early screening technology is expected to significantly reduce the screening cost of the tumors and greatly increase the early diagnosis rate of the tumors.

At present, the cancers that can be screened in clinical practice mainly include lung cancer, intestinal cancer, breast cancer, cervical cancer, gastric cancer, esophageal cancer, liver cancer, etc. However, for most other cancers, at present, a feasible early screening method is still lacked.

SUMMARY

To overcome the defects of the prior art, a purpose of the present application is to provide multi-cancer detection and traceability systems based on DNA high-throughput methylation sequencing. The multi-cancer detection and traceability systems based on DNA high-throughput methylation sequencing have the characteristics of non-invasive detection, low sequencing cost, high detection specificity and sensitivity, etc.

To achieve the above purpose, the present application provides the following solution:

A multi-cancer detection system based on high-throughput methylation sequencing of cell-free DNA includes:

a first sample sequencing module used for collecting cancer tissue and pericancerous tissue samples of a target cancer, and plasma samples of a target cancer patient and a healthy person, extracting a first genomic DNA of the cancer tissue and pericancerous tissue samples of the target cancer and a first cell-free DNA of the plasma samples of the target cancer patient and the healthy person, and performing methylation sequencing on the first genomic DNA and the first cell-free DNA respectively to obtain sequencing data of the first genomic DNA and sequencing data of the first cell-free DNA;

a first methylation feature set acquisition module used for mapping the sequencing data of the first genomic DNA and the sequencing data of the first cell-free DNA respectively to a human reference genome after quality control is performed on the sequencing data of the first genomic DNA and the sequencing data of the first cell-free DNA to obtain first coordinates of the sequencing data of the first genomic DNA and the sequencing data of the first cell-free DNA on the human reference genome; dividing the human reference genome into a plurality of CpG Island regions according to the first coordinates, and counting methylation levels of the sequencing data of the first genomic DNA about different preset haploid algorithms on the CpG Island regions; comparing differences in the methylation levels of the sequencing data of the first genomic DNA about different haploid algorithms on the CpG Island regions to obtain cancer-specific regions of the sequencing data of the first genomic DNA about each haploid algorithm; and counting the methylation levels of the sequencing data of the first genomic DNA about the different preset haploid algorithms on the cancer-specific regions to obtain a methylation feature set of the first cell-free DNA;

a first terminal motif feature acquisition module used for taking all base data of p base pairs of 3' terminal of the sequencing data of the first cell-free DNA on the human reference genome as a terminal motif base fragment set, and taking a proportion of each base fragment in the terminal motif base fragment set in a permutation and combination of all base sequences of the p base pairs as a terminal motif feature of the first cell-free DNA;

a first breakpoint motif feature acquisition module used for taking all base data of upstream and downstream q base pairs of the 3' terminal of the sequencing data of the first cell-free DNA on the human reference genome as a breakpoint motif base fragment set, and taking a proportion of each base fragment in the breakpoint motif base fragment set in a permutation and combination of all base sequences of 2*q base pairs as a breakpoint motif feature of the first cell-free DNA; and a detection model building module used for training a learning classification module by taking the methylation feature set of the first cell-free DNA, the terminal motif feature of the first cell-free DNA, and the breakpoint motif feature of the first cell-free DNA as input vectors, and whether cancer is suffered from as an output vector to obtain a trained multi-cancer detection model which is used for detecting whether a target object suffers from the target cancer.

A multi-cancer traceability system based on high-throughput methylation sequencing of cell-free DNA includes:

a second sample sequencing module used for collecting cancer tissue and pericancerous tissue samples of a target cancer, and a plasma sample of a target cancer patient, extracting a second genomic DNA of the cancer tissue and pericancerous tissue samples of the target cancer and a second cell-free DNA of the plasma sample of the target cancer patient, and performing methylation sequencing on the second genomic DNA and the second cell-free DNA respectively to obtain sequencing data of the second genomic DNA and sequencing data of the second cell-free DNA;

a second methylation feature set acquisition module used for mapping the sequencing data of the second genomic DNA and the sequencing data of the second cell-free DNA respectively to a human reference genome after quality control is performed on the sequencing data of the second genomic DNA and the sequencing data of the second cell-free DNA to obtain second coordinates of the sequencing data of the second genomic DNA and the sequencing data of the second cell-free DNA on the human reference genome; dividing the human reference genome into a plurality of CpG Island regions according to the second coordinates, and counting methylation levels of the sequencing data of the second genomic DNA about different haploid algorithms on the CpG Island regions; comparing differences in the methylation levels of the sequencing data of the second genomic DNA about preset haploid algorithms on the CpG Island regions to obtain tissue-specific regions of the sequencing data of the second genomic DNA about each haploid algorithm; and counting the methylation levels of the sequencing data of the second genomic DNA about the preset haploid algorithms on the tissue-specific regions to obtain a methylation feature set of the second cell-free DNA;

a second terminal motif feature acquisition module used for taking all base data of p base pairs of 3' terminal of the sequencing data of the second cell-free DNA on the human reference genome as a terminal motif base fragment set, and taking a proportion of each base fragment in the terminal motif base fragment set in a permutation and combination of all base sequences of the p base pairs as a terminal motif feature of the second cell-free DNA;

a second breakpoint motif feature acquisition module used for taking all base data of upstream and downstream q base pairs of the 3' terminal of the sequencing data of the second cell-free DNA on the human reference genome as a breakpoint motif base fragment set, and taking a proportion of each base fragment in the breakpoint motif base fragment set in a permutation and combination of all base sequences of $2*q$ base pairs as a breakpoint motif feature of the second cell-free DNA; and a traceability model building module used for training a learning classification module by taking the methylation feature set of the second cell-free DNA, the terminal motif feature of the second cell-free DNA, and the breakpoint motif feature of the second cell-free DNA as input vectors, and a probability of suffering from a cancer as an output vector to obtain a trained multi-cancer traceability model which is used for judging types of a detected cancer.

BRIEF DESCRIPTION OF THE DRAWINGS

FIG. 3(*b*) shows mapping rates; FIG. 3(*c*) is a chart of the number of reads mapped to a reference genome; FIG. 3(*d*) is a chart of the number of CGI islands covering more than 10×; and FIG. 3(*e*) is a chart of the number of CpG sites covering more than 10×;

FIG. 7(*b*) is a sensitivity chart of a model at different stages of colorectal cancer; FIG. 7(*c*) is a sensitivity chart of the model at different stages of gastric cancer; FIG. 7(*d*) is a sensitivity chart of the model at different stages of liver cancer; FIG. 7(*e*) is a sensitivity chart of the model at different stages of thyroid cancer, and FIG. 7(*f*) is a sensitivity chart of the model at different stages of breast cancer;

DETAILED DESCRIPTION

The purpose of the present application is to provide multi-cancer detection and traceability systems based on DNA high-throughput methylation sequencing. The multi-cancer detection and traceability systems based on DNA high-throughput methylation sequencing have the characteristics of non-invasive detection, low sequencing cost, high detection specificity and sensitivity, etc.

To make the above purpose, features and advantages of the present application more obvious and understandable, the present application is further described in detail below in combination with the drawings and specific embodiments.

Figure 1:
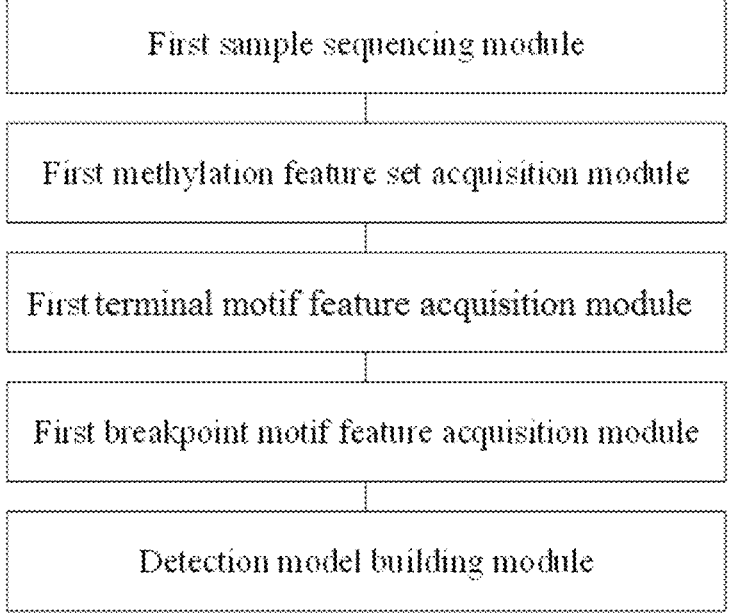
FIG. 1 shows a building process of a detection model provided by an embodiment of the present application.

FIG. 1 shows a building process of a detection model. As shown in FIG. 1, the present application provides a multi-cancer detection system based on high-throughput methylation sequencing of cell-free DNA, including:

a first sample sequencing module used for collecting cancer tissue and pericancerous tissue samples of a target cancer, and plasma samples of a target cancer patient and a healthy person, extracting a first genomic DNA of the cancer tissue and pericancerous tissue samples of the target cancer and a first cell-free DNA of the plasma samples of the target cancer patient and the healthy person, and performing methylation sequencing on the first genomic DNA and the first cell-free DNA respectively to obtain sequencing data of the first genomic DNA and sequencing data of the first cell-free DNA;

a first methylation feature set acquisition module used for mapping the sequencing data of the first genomic DNA and the sequencing data of the first cell-free DNA respectively to a human reference genome after quality control is performed on the sequencing data of the first genomic DNA and the sequencing data of the first cell-free DNA to obtain first coordinates of the sequencing data of the first genomic DNA and the sequencing data of the first cell-free DNA on the human reference genome; dividing the human reference genome into a plurality of CpG Island regions according to the first coordinates, and counting methylation levels of the sequencing data of the first genomic DNA about different preset haploid algorithms on the CpG Island regions; comparing differences in the methylation levels of the sequencing data of the first genomic DNA about different haploid algorithms on the CpG Island regions to obtain cancer-specific regions of the sequencing data of the first genomic DNA about each haploid algorithm; and counting the methylation levels of the sequencing data of the first genomic DNA about the different preset haploid algorithms on the cancer-specific regions to obtain a methylation feature set of the first cell-free DNA;

a first terminal motif feature acquisition module used for taking all base data of p base pairs of 3' terminal of the sequencing data of the first cell-free DNA on the human reference genome as a terminal motif base fragment set, and taking a proportion of each base fragment in the terminal motif base fragment set in a permutation and combination of all base sequences of the p base pairs as a terminal motif feature of the first cell-free DNA;

a first breakpoint motif feature acquisition module used for taking all base data of upstream and downstream q base pairs of the 3' terminal of the sequencing data of the first cell-free DNA on the human reference genome as a breakpoint motif base fragment set, and taking a proportion of each base fragment in the breakpoint motif base fragment set in a permutation and combination of all base sequences of 2*q base pairs as a breakpoint motif feature of the first cell-free DNA; and a detection model building module used for training a learning classification module by taking the methylation feature set of the first cell-free DNA, the terminal motif feature of the first cell-free DNA, and the breakpoint motif feature of the first cell-free DNA as input vectors, and whether cancer is suffered from as an output vector to obtain a trained multi-cancer detection model which is used for detecting whether a target object suffers from the target cancer.

Optionally, a computer-readable medium is provided, and the computer-readable medium can run a computer program used in the multi-cancer detection system based on high-throughput methylation sequencing of cell-free DNA.

Specifically, the target cancer includes lung cancer, gastric cancer, colorectal cancer, liver cancer, breast cancer and thyroid cancer.

Optionally, the preset haploid algorithms include MM, MHL, CHALM, PDR and Entropy.

Further, the first sample sequencing module includes:

a first sample collection unit used for collecting 10 ml of whole blood samples of the target cancer patient and the healthy person respectively by using cell-free DNA blood collection tubes;

a cell-free DNA extraction unit used for extracting the first cell-free DNA from the whole blood samples after plasma separation by using a GENFINE® plasma DNA extraction kit; and a cell-free DNA sequencing unit used for building a library and degenerating representative bisulfite sequencing for the first cell-free DNA to obtain the sequencing data of the first cell-free DNA.

Further, the first sample sequencing module further includes:

a second sample collection unit used for collecting the cancer tissue and pericancerous tissue samples of the target cancer;

a genomic DNA extraction unit used for extracting the first genomic DNA from the cancer tissue and pericancerous tissue samples of the target cancer by using a TIANGEN® genomic DNA extraction kit; and a genomic DNA sequencing unit used for building a library and degenerating representative bisulfite sequencing for the first genomic DNA to obtain the sequencing data of the first genomic DNA.

Specifically, the first methylation feature set acquisition module includes:

a control group setting unit used for taking samples of each cancer in the target cancer as a positive control group respectively, and taking pericancerous samples corresponding to the target cancer as a negative control group; and a control group comparison unit used for comparing P values of the methylation levels of the positive control group and the negative control group about the haploid algorithms after multiple test and correction to obtain the cancer-specific regions of all target cancer samples.

Specifically, the learning classification module includes a first sub-module and a second sub-module connected with the first sub-module, and ensemble algorithms are embedded into the first sub-module; the ensemble algorithms include: a logistic regression model algorithm, a support vector machine algorithm, a random forest algorithm, a gradient boosting tree algorithm, a Bayesian model algorithm, a K-nearest neighbor algorithm, an XGBoost algorithm and a CatBoost algorithm; the second sub-module is built-in with a logistic regression model; the ensemble algorithms are used for training the methylation feature set of the cell-free DNA, the terminal motif feature of the cell-free DNA, and the breakpoint motif feature of the cell-free DNA; and the logistic regression model is used for integrating and outputting training results of the ensemble algorithms.

Optionally, the p is any integer between 4 and 10, and the q is any integer between 2 and 5.

Figure 2:
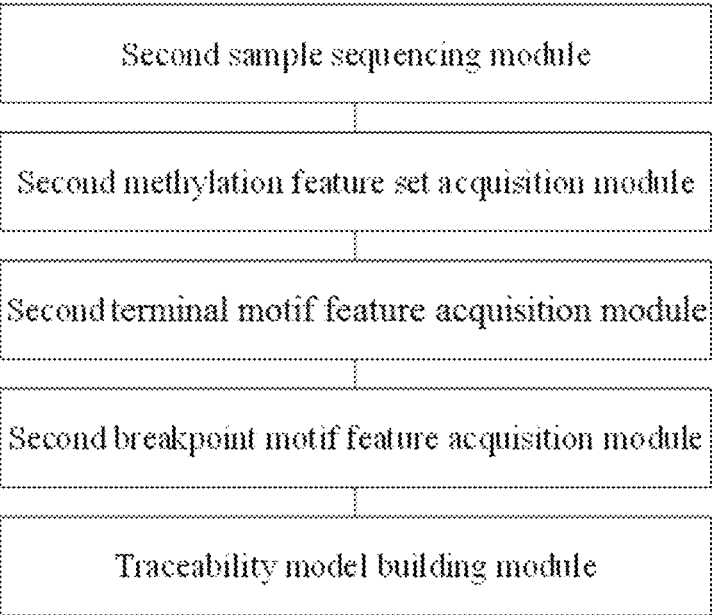
FIG. 2 shows a building process of a traceability model provided by an embodiment of the present application.
Figures 3A, 3B:
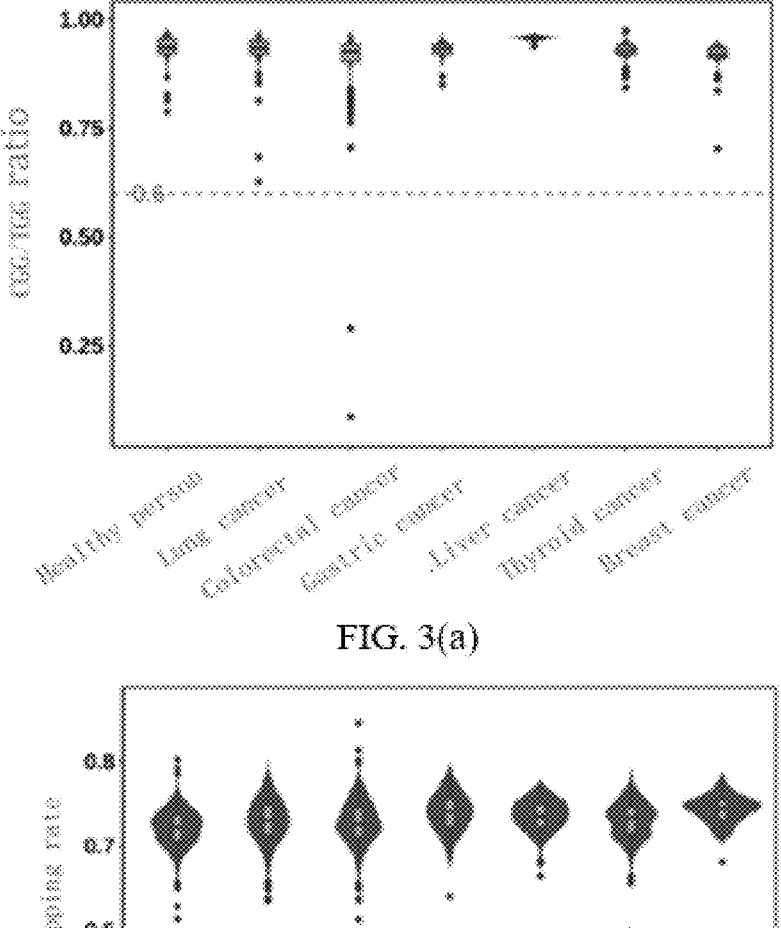
FIG. 3(*a*) is a CGG/TGG ratio chart.
Figure 3C:
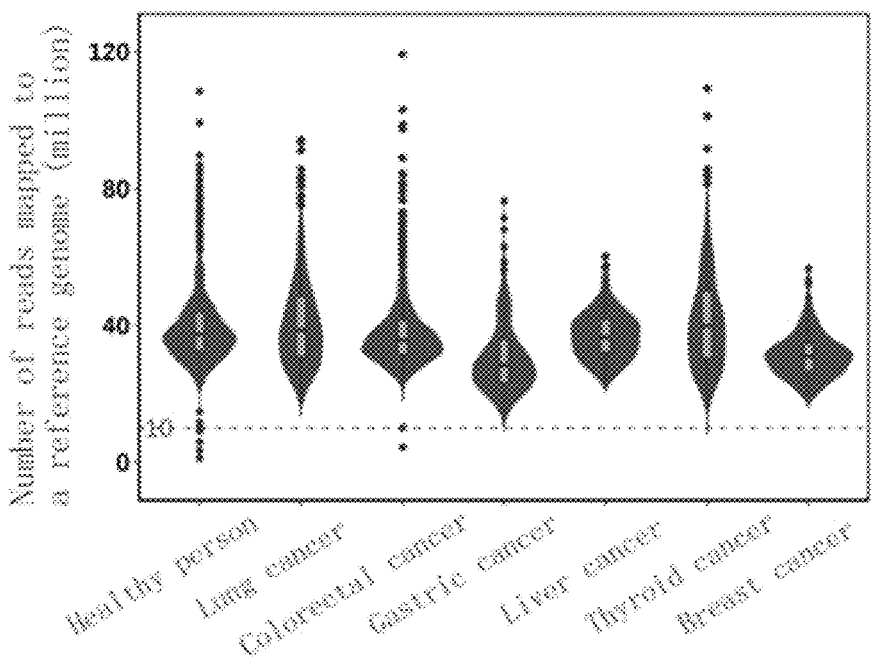
Figure 3D:
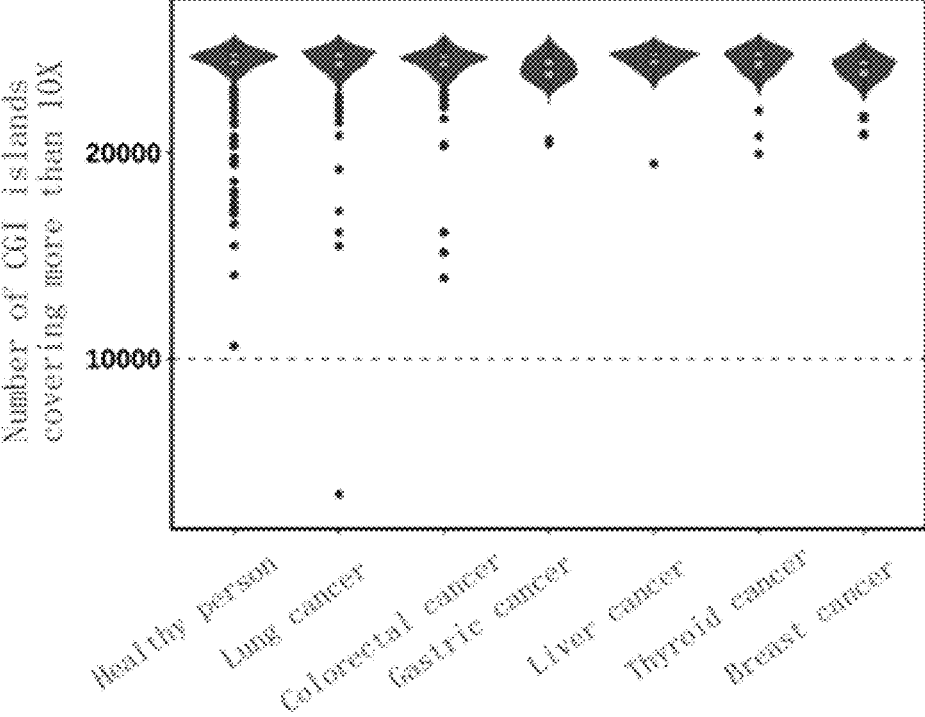
Figure 3E:
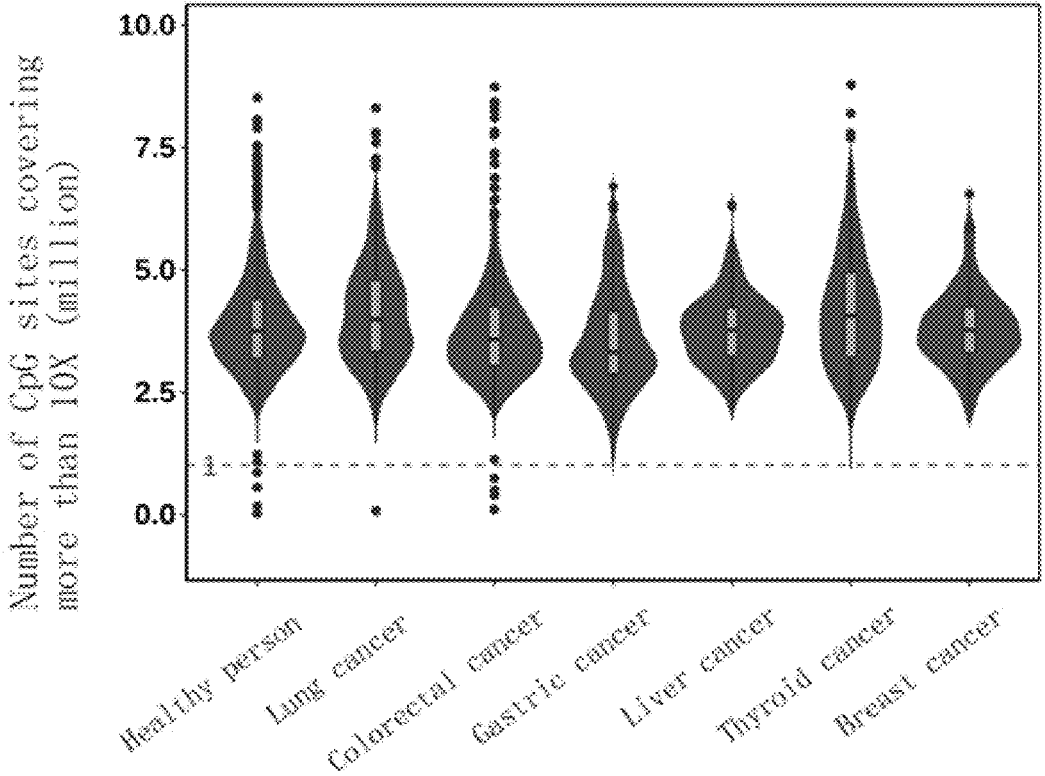

FIG. 2 shows a building process of a traceability model. As shown in FIG. 2, the present application provides a multi-cancer traceability system based on high-throughput methylation sequencing of cell-free DNA, including:

a second sample sequencing module used for collecting cancer tissue and pericancerous tissue samples of a target cancer, and a plasma sample of a target cancer patient, extracting a second genomic DNA from the cancer tissue and pericancerous tissue samples of the target cancer and a second cell-free DNA of the plasma sample of the target cancer patient, and performing methylation sequencing on the second genomic DNA and the second cell-free DNA respectively to obtain sequencing data of the second genomic DNA and sequencing data of the second cell-free DNA;

a second methylation feature set acquisition module used for mapping the sequencing data of the second genomic DNA and the sequencing data of the second cell-free DNA respectively to a human reference genome after quality control is performed on the sequencing data of the second genomic DNA and the sequencing data of the second cell-free DNA to obtain second coordinates of the sequencing data of the second genomic DNA and the sequencing data of the second cell-free DNA on the human reference genome; dividing the human reference genome into a plurality of CpG Island regions according to the second coordinates, and counting methylation levels of the sequencing data of the second genomic DNA about different haploid algorithms on the CpG Island regions; comparing differences in the methylation levels of the sequencing data of the second genomic DNA about preset haploid algorithms on the CpG Island regions to obtain tissue-specific regions of the sequencing data of the second genomic DNA about each haploid algorithm; and counting the methylation levels of the sequencing data of the second genomic DNA about the preset haploid algorithms on the tissue-specific regions to obtain a methylation feature set of the second cell-free DNA;

a second terminal motif feature acquisition module used for taking all base data of p base pairs of 3' end of the sequencing data of the second cell-free DNA on the human reference genome as a terminal motif base fragment set, and taking a proportion of each base fragment in the terminal motif base fragment set in a permutation and combination of all base sequences of the p base pairs as a terminal motif feature of the second cell-free DNA;

a second breakpoint motif feature acquisition module used for taking all base data of upstream and downstream q base pairs of the 3' terminal of the sequencing data of the second cell-free DNA on the human reference genome as a breakpoint motif base fragment set, and taking a proportion of each base fragment in the breakpoint motif base fragment set in a permutation and combination of all base sequences of 2*q base pairs as a breakpoint motif feature of the second cell-free DNA; and a traceability model building module used for training a learning classification module by taking the methylation feature set of the second cell-free DNA, the terminal motif feature of the second cell-free DNA, and the breakpoint motif feature of the second cell-free DNA as input vectors, and a probability of suffering from a cancer as an output vector to obtain a trained multi-cancer traceability model which is used for judging types of a detected cancer.

Specifically, the present embodiment further provides a cancer detection method for distinguishing whether a sample suffers from lung cancer, gastric cancer, colorectal cancer, liver cancer, breast cancer and thyroid cancer, including the following steps:

collecting cancer tissue and pericancerous tissue samples of a target cancer, extracting a genomic DNA of the cancer tissue and pericancerous tissue samples of the target cancer and performing methylation sequencing on the genomic DNA to obtain sequencing data of the cancer tissue and pericancerous tissue samples;

mapping the sequencing data of the cancer tissue and pericancerous tissue samples to a human reference genome after quality control is performed on the sequencing data of the cancer tissue and pericancerous tissue samples to obtain coordinates of the sequencing data of the cancer tissue and pericancerous tissue samples on the human reference genome; dividing the human reference genome into a plurality of CpG Island regions according to the coordinates of the sequencing data of the cancer tissue and pericancerous tissue samples on the human reference genome, and counting methylation levels of the sequencing data of the cancer tissue and pericancerous tissue samples about different haploid algorithms on the CpG Island regions;

comparing differences in the methylation levels of the sequencing data of the cancer tissue and pericancerous tissue samples about each haploid algorithm on the CpG Island regions to obtain cancer-specific regions of the sequencing data of the cancer tissue and pericancerous tissue samples about each haploid algorithm;

collecting plasma samples of a target cancer patient and a healthy person, extracting a cell-free DNA of the plasma samples of the target cancer patient and the healthy person and performing methylation sequencing on the cell-free DNA to obtain sequencing data of the plasma samples of the target cancer patient and the healthy person;

mapping the plasma samples of the target cancer patient and the healthy person to the human reference genome after quality control is performed on the sequencing data of the plasma samples of the target cancer patient and the healthy person to obtain coordinates of the sequencing data of the plasma samples of the target cancer patient and the healthy person on the human reference genome; and counting methylation levels of the sequencing data of the target cancer patient and the healthy person about the haploid algorithms on the cancer-specific regions according to the coordinates of the sequencing data of the plasma samples of the target cancer patient and the healthy person on the human reference genome to obtain a methylation feature set of the target cancer patient and the healthy person;

taking all base data of p base pairs of 3' terminal of the sequencing data of the plasma samples of the target cancer patient and the healthy person on the human reference genome as a terminal motif base fragment set, and taking a proportion of each base fragment in the terminal motif base fragment set in a permutation and combination of all base sequences of the p base pairs as a terminal motif feature of the target cancer patient and the healthy person;

taking all base data of upstream and downstream q base pairs of the 3' terminal of the sequencing data of the plasma samples of the target cancer patient and the healthy person on the human reference genome as a breakpoint motif base fragment set, and taking a proportion of each base fragment in the breakpoint motif base fragment set in a permutation and combination of all base sequences of 2*q base pairs as a breakpoint motif feature of the target cancer patient and the healthy person;

training a learning classification module by taking the methylation feature set of the target cancer patient and the healthy person, the terminal motif feature of the target cancer patient and the healthy person, and the breakpoint motif feature of the target cancer patient and the healthy person as input vectors, and whether cancer is suffered from as an output vector to obtain a trained multi-cancer detection model which is used for detecting lung cancer, gastric cancer, colorectal cancer, liver cancer, breast cancer and thyroid cancer.

By referring to FIG. 3(a)-FIG. 3(e), quality control requirements are as follows: the ratio of CGG/TGG is greater than 0.6, the mapping rate is greater than 0.4, the number of reads mapped to the human reference genome is greater than 10 million, the number of CGI islands covering more than 10× is greater than 10,000 and the number of CpG sites covering more than 10× is greater than 1 million.

Specifically, the cell-free DNA is also called cfDNA; the genomic DNA is also called gDNA; the terminal motif feature is also called 6-mer EndMotif; the breakpoint motif feature is also called 6-mer Breakpoint motif; the logistic regression model is also called Logistic Regression, abbreviated as LR; the support vector machine is abbreviated as SVM; the random forest is abbreviated as RF; the gradient boosting tree algorithm is also called Gradient Boosting Machine, abbreviated as GBM; a Bayesian model is also called Naïve Bayes, abbreviated as NB; the K-nearest neighbor algorithm is also called K-Nearest Neighbor, abbreviated as KNN Further, library building for the cell-free DNA sample adopts a patent technology: a method for rapidly building an RRBS sequencing library using circulating tumor DNA in blood, with patent number: ZL 2021 1 1060927.0.

Specifically, each haploid algorithm is an algorithm for calculating the methylation level in a region. Due to the differences in the algorithms of different haploids, the methylation levels obtained from the same sequencing data are also different. A model is built by performing machine learning on the methylation levels of the sequencing data under different haploid algorithms. Different cancers can be distinguished by using the model. By comparing the haploid methylation levels of the cancer tissue samples and the pericancerous tissue samples, sequencing data fragments with significant differences on the regions of different CpG islands are determined, and the corresponding sequencing data fragments can be used as distinguishing features.

Optionally, in tumor tissues, due to changes in chromatin states, abnormal nuclease activity, etc., DNA fragments cleaved at tumor-specific sites can be obtained. Because the position of a breakpoint is specific, the proportion of the end terminal sequence is different.

Further, a calculation mode of the terminal motif feature includes: mapping the high-throughput sequencing data of cell-free DNA to the human reference genome, and extracting 6 base sequences corresponding to the 3' terminal position of each read segment data on the human reference genome. The direction of the base sequences is the direction from 5' to 3' terminal. Each base sequence can be A, T, C or G. There are 4096 possible permutations and combinations of the 6 base sequences. Therefore, there are 4096 terminal motif proportions.

Further, a calculation mode of the breakpoint motif feature includes: mapping the high-throughput sequencing data of cell-free DNA to the human reference genome, and extracting upstream and downstream 3 base sequences corresponding to the 3' terminal position of each read segment data on the human reference genome. The direction of the base sequences is the direction from the 5' to 3' terminal. Each base sequence can be A, T, C or G. There are 4096 possible permutations and combinations of 6 base sequences. Therefore, there are 4096 breakpoint motif proportions.

Specifically, logistic regression, also called logistic regression analysis, is a generalized logistic regression analysis model and belongs to supervised learning in machine learning. The process of logistic regression is as follows: establishing a cost function in the face of classification problems, and solving an optimal model parameter through iteration of an optimization method. The method has the advantages of high speed, suitability for binary classification problems, simplicity and easy understanding.

Specifically, the support vector machine model is a supervised learning algorithm used for predicting discrete or continuous variables. The model maps a data set to a high-dimensional space and finds an optimal hyperplane to maximize intervals between data points of different categories, so as to achieve classification or regression. During training, set parameters are: kernel="linear", scale=T, probability=TRUE, and type="C-classification".

Specifically, the random forest model is a supervised learning algorithm used for predicting discrete or continuous variables. The model builds a plurality of decision tree models by randomly selecting features and subsets of the data set, and averages or votes prediction results to improve the accuracy of the prediction. During training, set parameters are: method="rf", prox=TRUE, ntree=500, and metric="Accuracy".

Specifically, the gradient boosting tree model is an ensemble learning algorithm that combines two techniques of gradient boosting and a decision tree. In the field of machine learning, the gradient boosting tree model is generally used for solving regression and classification problems. The gradient boosting tree model has the main advantages of processing mixed data types and being robust to outliers and noisy data. During training, set parameters are: method='gbm', and trControl=trainControl (allowParallel=TRUE, verboseIter=FALSE).

Specifically, the Bayesian model is a statistical model based on the Bayes' Theorem, and is used for processing uncertainty and probability inference problems. The Bayesian model uses probability distribution to describe parameters or unknowns, updates the probability distribution of the parameters according to the observed data, and is suitable for problems in various fields of regression analysis, classification, clustering, etc. During training, set parameters are: laplace=0, and type='row'.

Specifically, XGBoost is an additive model based on a boosting tree and is one of gradient boosting decision trees. The basic idea of XGBoost is the same as that of the gradient boosting decision tree, but XGBoost adds many optimizations. Each base classifier used by XGBoost is a regression tree, and a training mode adopts a forward stagewise algorithm algorithm to gradually optimize each base learner therein. During training, set parameters are: nrounds=1000, and params=list (booster="gbtree", objective="binary: logistic", eval_metric="logloss").

Specifically, the K-nearest neighbor algorithm is a simple and effective supervised learning algorithm used for classification and regression problems. The basic idea is: if the majority of K nearest neighbors of a sample in a feature space belong to classification problems or regression problems, then the sample also belongs to this category or has this mean value. During training, set parameters are: k=seq (1,30,2), method='repeatedcv', and number=10.

Specifically, CatBoost is a gradient boosting decision tree framework implemented based on a symmetric decision tree as a base learner, with fewer parameters, support for categorical variables and high accuracy. CatBoost is composed of Categorical and Boosting, and aims to solve the problems of gradient bias and prediction offset, so as to reduce the occurrence of overfitting, thereby improving the accuracy and generalization ability of the algorithm. During training, set parameters are: params=list (loss_function='Logloss', iterations=1000).

Further, all the plasma samples are randomly divided into a training set and a validation set at a ratio of 1:1. The training set is used for training the model, and the validation set is used for evaluating the model.

Optionally, the features of a multi-cancer early screening model include: MM, MHL, CHALM, PDR, Entropy, a terminal motif feature and a breakpoint motif feature. The samples of the training set are inputted into 8 machine learning algorithm models for training respectively, and finally a probability value of suffering from a cancer is taken as an output result. Therefore, each feature is trained by 8 machine learning models, with a total of 56 machine learning models, which is the training model of a first unit. The training results of 56 machine learning models in a first layer are inputted into a logistic regression model of a second unit for integration, and the probability value of suffering from a cancer is taken as the final model result for multi-cancer early screening. This method is called a stack ensemble machine learning model. The model uses meta-learning algorithms to learn how to best combine predictions from two or more basic machine learning algorithms. The advantage of the solution is that the capabilities of a series of models with good performance in classification or regression tasks can be used and better predictions than any model in the integration can be made.

Figure 4:
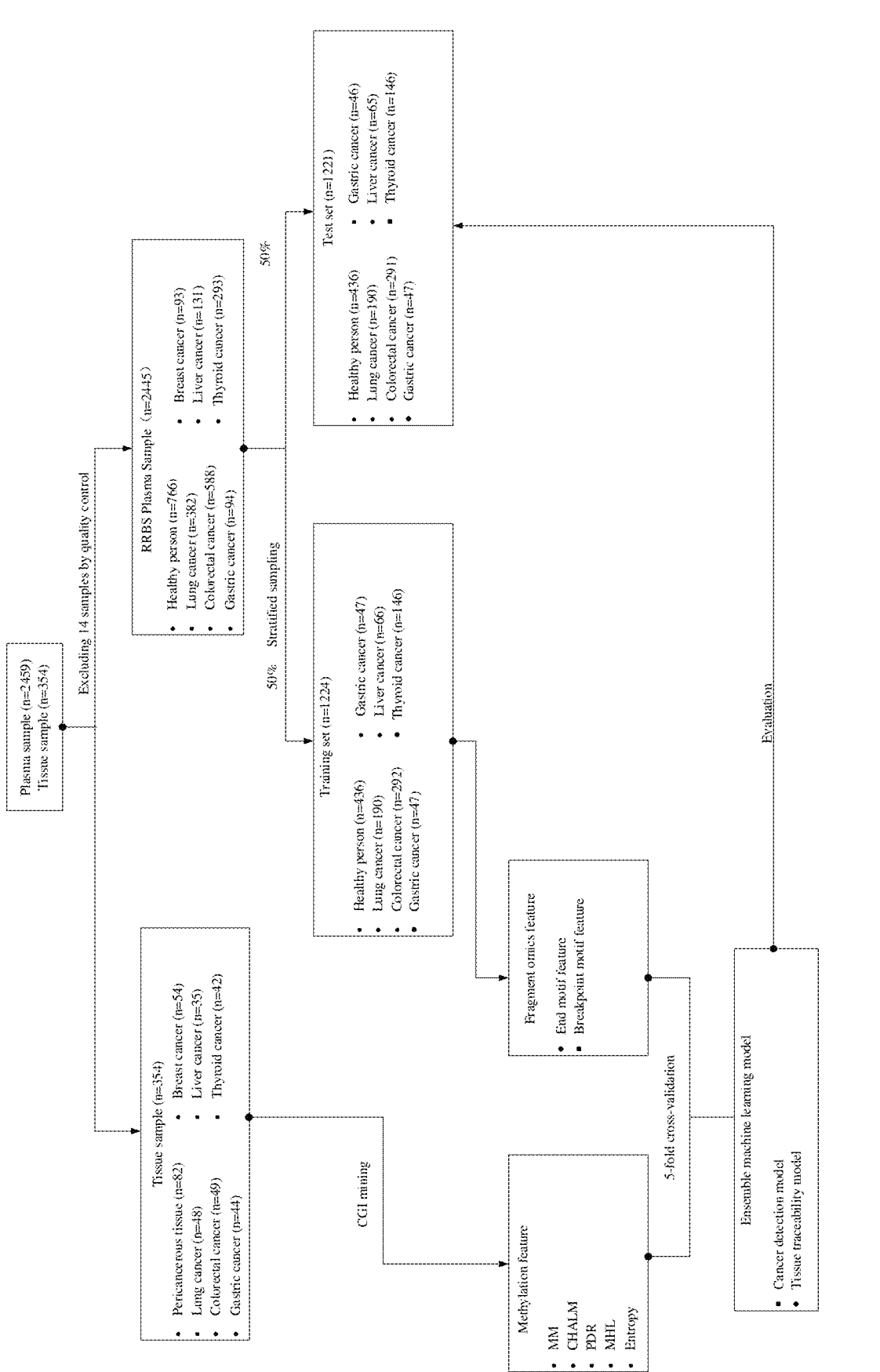
FIG. 4 shows a specific building process of a learning model provided by an embodiment of the present application.

By referring to FIG. 4, to better train and evaluate the model, the present application collects a large number of plasma samples, with a total of 2459 samples. After quality control, 2445 samples are retained. The 2445 samples are randomly divided into a training set and a validation set at a ratio of 1:1. The training set is used for training the model, and the validation set is used for evaluating the model.

The results of the training set and the validation set are shown in Table 1:

1224 cases in the training set are used for training the model. The specificity of the obtained model is 95.18%, the sensitivity is 88.58%, and the accuracy is 90.93%.

1221 cases in the validation set are used for evaluating the model. The specificity of the model is 96.33%, the sensitivity is 91.21%, and the accuracy is 93.04%.

The specificity, the sensitivity and the accuracy of the training set and the validation set are almost the same. The model training is good and no obvious overfitting occurs.

TABLE 1

Specificity, Sensitivity and Accuracy of
Training Set and Validation set

| | Predicted total number | Cancer samples | Samples of healthy person |
|---|---|---|---|
| Training set | | | |
| Total number of samples | 1224 | 788 | 436 |
| Predicted cancer | 719 | 698 | 21 |
| Predicted healthy person | 505 | 90 | 415 |
| Specificity | — | — | 95.18% |
| Sensitivity | — | 88.58% | — |
| Accuracy | | 90.93% | |
| Validation set | | | |
| Total number of samples | 1221 | 785 | 436 |
| Predicted cancer | 732 | 716 | 16 |
| Predicted healthy person | 489 | 69 | 420 |
| Specificity | | — | 96.33% |
| Sensitivity | — | 91.21% | — |
| Accuracy | | 93.04% | |

Figure 5:
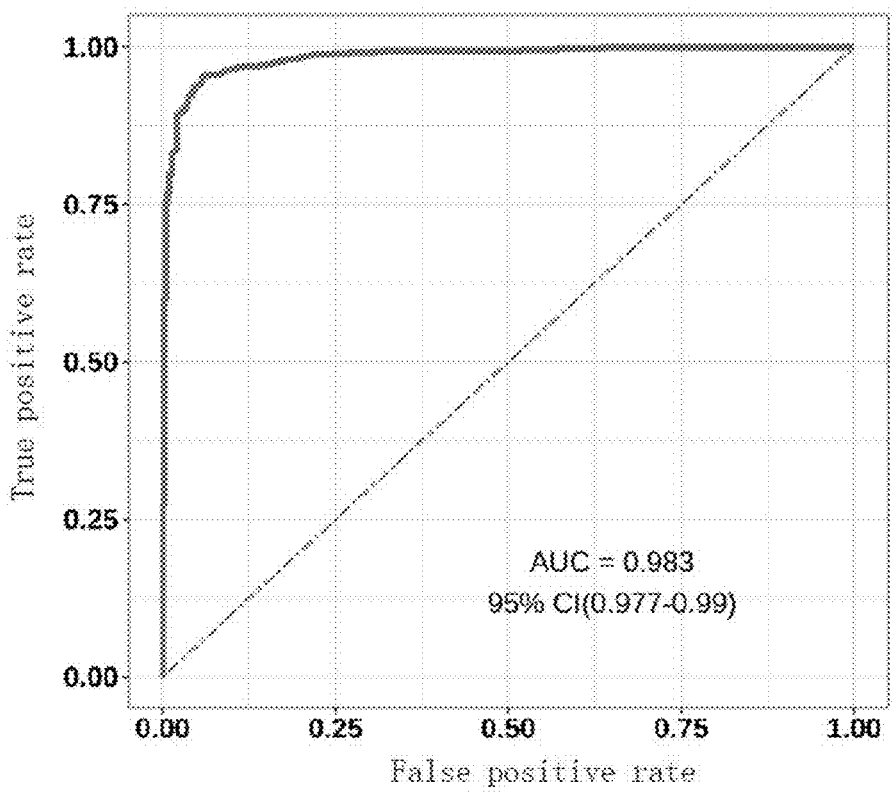
FIG. 5 is an AUC presentation chart provided by an embodiment of the present application.
Figure 6:
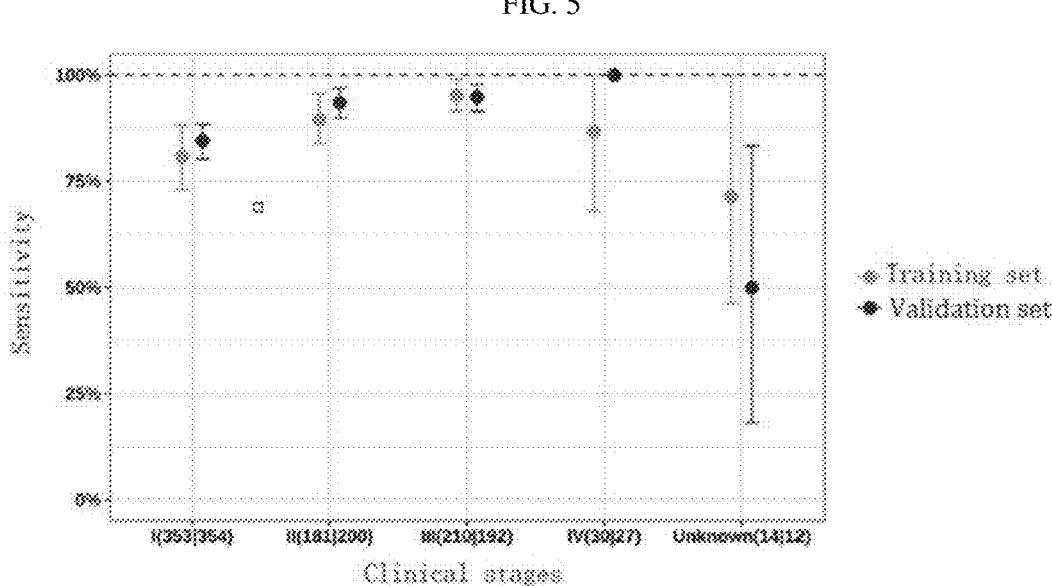
FIG. 6 is a sensitivity chart at different stages provided by an embodiment of the present application.
Figure 7A:
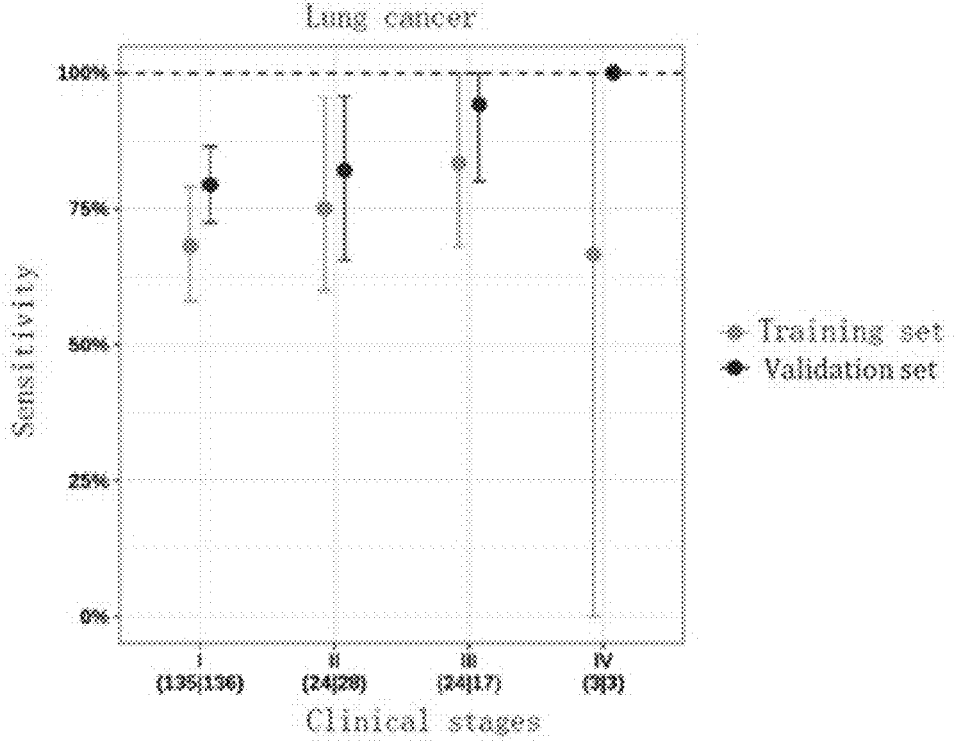
FIG. 7(*a*) is a sensitivity chart at different stages of lung cancer.
Figure 7B:
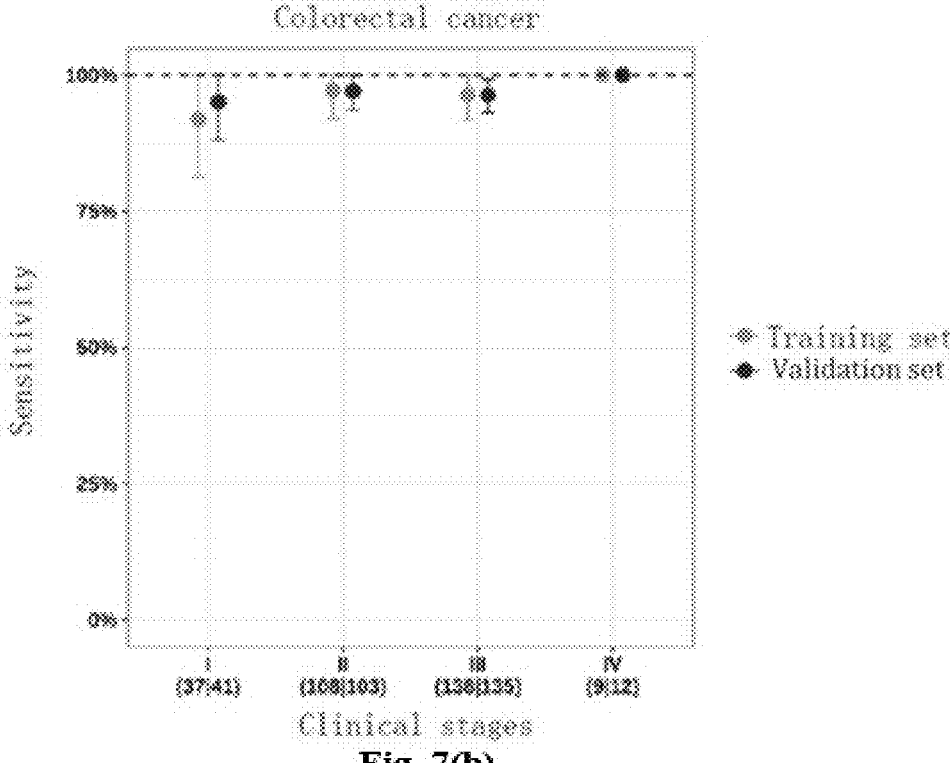
Figure 7C:
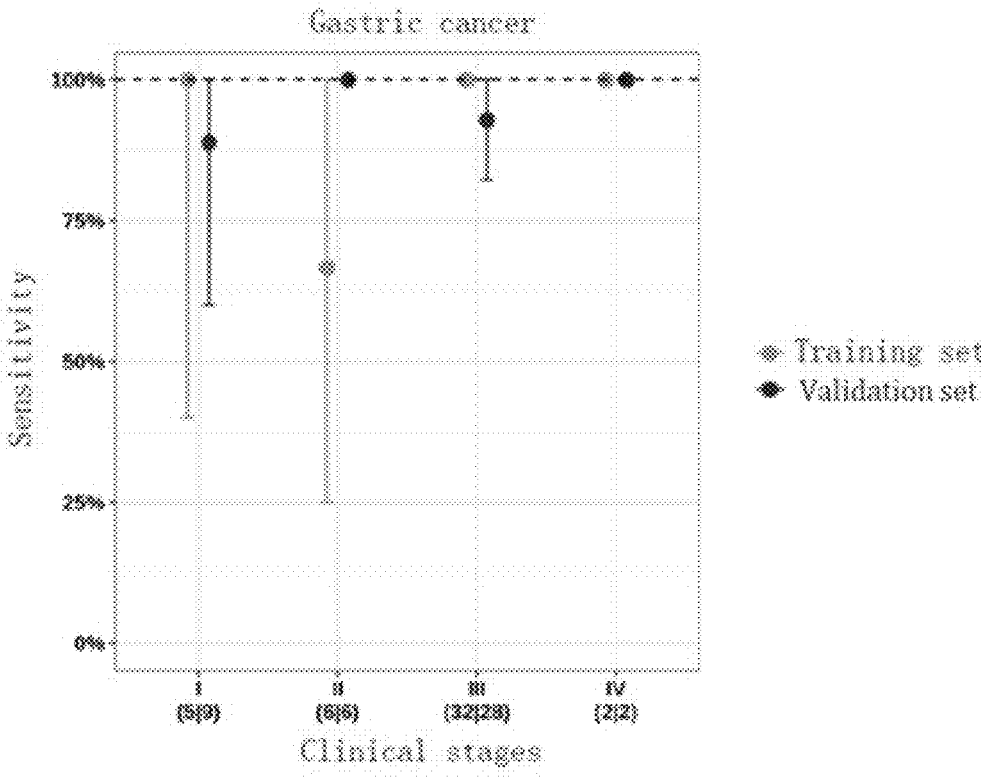
Figure 7D:
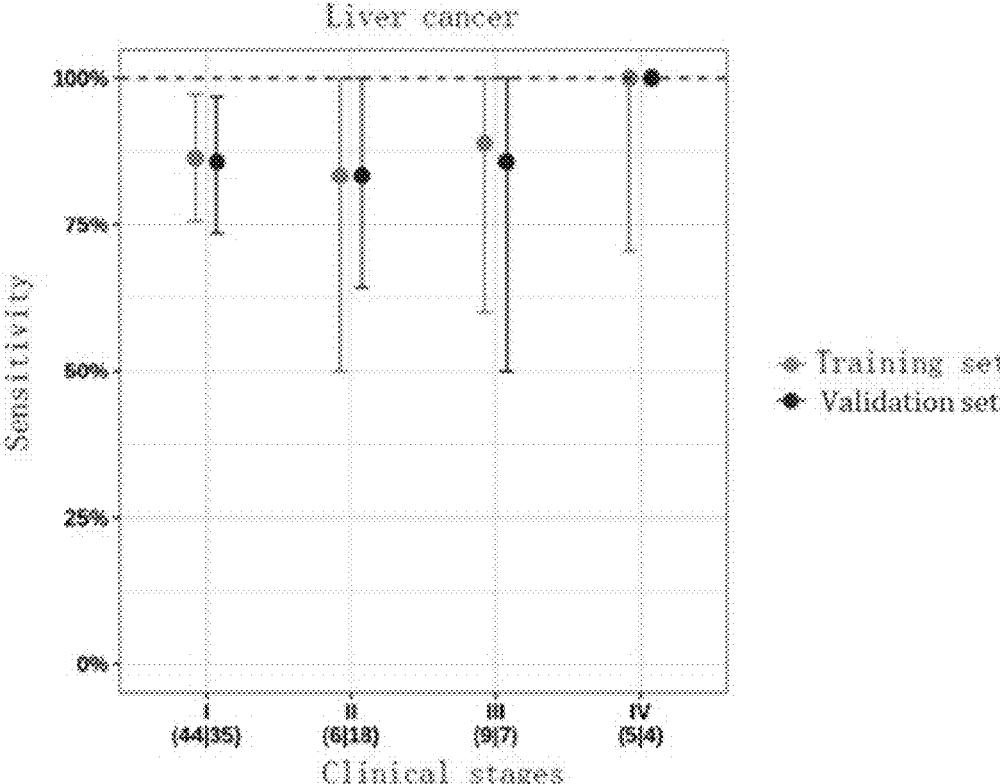
Figure 7E:
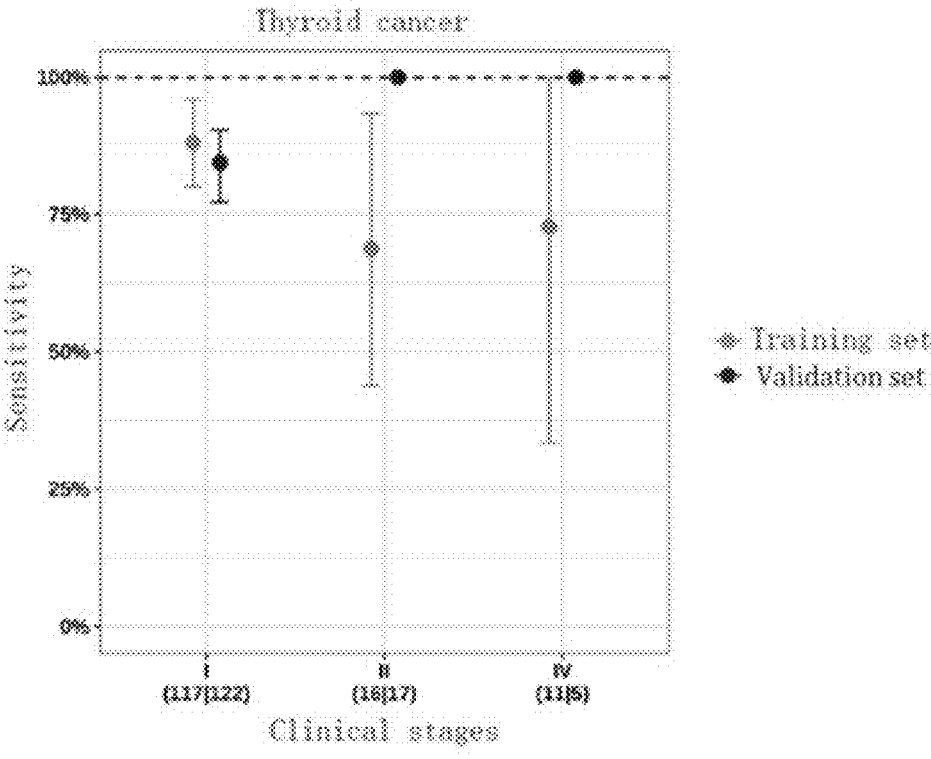
Figure 7F:
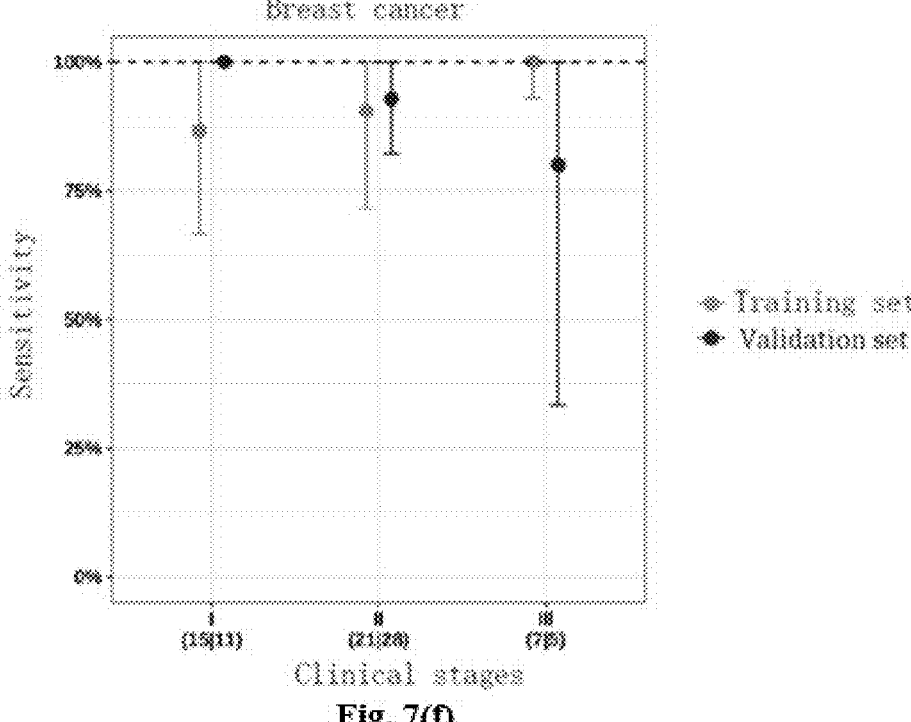

By referring to FIG. 5, the obtained AUC on the validation set is 0.983, which indicates that the present embodiment has excellent prediction performance.

By referring to FIG. 6 and FIG. 7(a)-FIG. 7(f), the sensitivity at different cancer stages is shown in Table 2.

The sensitivity of the model at different stages conforms to the normal law, and is lower in stages I and II, and higher in stages III and IV. Even in the early stage I of the cancer, the sensitivity of the model remains high, and can reach 91% for colorectal cancer.

TABLE 2

Sensitivity at Different Cancer Stages

| Cancer types | I | II | III | IV |
|---|---|---|---|---|
| Training set | | | | |
| Lung cancer | 71.11% | 79.17% | 91.67% | 66.67% |
| Colorectal cancer | 91.89% | 98.15% | 97.10% | 100.00% |
| Gastric cancer | 60.00% | 66.67% | 100.00% | 100.00% |
| Liver cancer | 93.18% | 100.00% | 88.89% | 100.00% |
| Thyroid cancer | 91.45% | 62.50% | | 72.73% |
| Breast cancer | 93.33% | 90.48% | 100.00% | |
| Validation set | | | | |
| Lung cancer | 80.88% | 85.71% | 94.12% | 100.00% |
| Colorectal cancer | 95.12% | 98.06% | 97.04% | 100.00% |
| Gastric cancer | 88.89% | 100.00% | 96.43% | 100.00% |
| Liver cancer | 94.29% | 94.44% | 85.71% | 100.00% |
| Thyroid cancer | 86.07% | 100.00% | | 100.00% |
| Breast cancer | 100.00% | 100.00% | 80.00% | 100.00% |

Specifically, the accuracy under different cancers are shown in Table 3:

The accuracy of the model under different cancers is high, with no obvious bias. The accuracy for colorectal cancer is the highest, and reaches 96.92% on the training set and 97.25% on the validation set.

TABLE 3

Accuracy Under Different Cancers

| Cancer types | Incorrect classification | Correct classification | Total | Accuracy |
|---|---|---|---|---|
| Training set | | | | |
| Lung cancer | 51 | 139 | 190 | 73.16% |
| Colorectal cancer | 9 | 283 | 292 | 96.92% |
| Gastric cancer | 4 | 43 | 47 | 91.49% |
| Liver cancer | 4 | 62 | 66 | 93.94% |
| Thyroid cancer | 19 | 127 | 146 | 86.99% |
| Breast cancer | 3 | 44 | 47 | 93.62% |
| Validation set | | | | |
| Lung cancer | 35 | 155 | 190 | 81.58% |
| Colorectal cancer | 8 | 283 | 291 | 97.25% |
| Gastric cancer | 3 | 44 | 47 | 93.62% |
| Liver cancer | 4 | 61 | 65 | 93.85% |
| Thyroid cancer | 17 | 129 | 146 | 88.36% |
| Breast cancer | 2 | 44 | 46 | 95.65% |

Specifically, the situations of tissue traceability are shown in Table 4:

The tissue traceability rate of the model is 71.83% on the training set, and 77.23% on the validation set, and the tissue can be well traced to specific cancers.

TABLE 4

| | | | Accuracy of Tissue Traceability | | | | |
| --- | --- | --- | --- | --- | --- | --- | --- |
| | | Actual | | | | | |
| Training set | Predicted | Lung cancer | Colorectal cancer | Gastric cancer | Liver cancer | Thyroid cancer | Breast cancer |
| | Lung cancer | 124 | 27 | 8 | 4 | 40 | 13 |
| | Colorectal cancer | 34 | 252 | 13 | 7 | 11 | 5 |
| | Gastric cancer | 2 | 1 | 18 | 0 | 2 | 2 |
| | Liver cancer | 2 | 2 | 0 | 55 | 0 | 0 |
| | Thyroid cancer | 22 | 8 | 2 | 0 | 93 | 3 |
| | Breast cancer | 6 | 2 | 6 | 0 | 0 | 24 |
| | Total | | | 788 | | | |
| | Accuracy | | | 71.83% | | | |
| | | Actual | | | | | |
| Validation set | Predicted | Lung cancer | Colorectal cancer | Gastric cancer | Liver cancer | Thyroid cancer | Breast cancer |
| | Lung cancer | 108 | 14 | 6 | 11 | 31 | 10 |
| | Colorectal cancer | 21 | 259 | 10 | 6 | 8 | 1 |
| | Gastric cancer | 4 | 4 | 28 | 0 | 2 | 1 |
| | Liver cancer | 0 | 0 | 0 | 44 | 0 | 0 |
| | Thyroid cancer | 9 | 3 | 0 | 0 | 85 | 3 |
| | Breast cancer | 13 | 3 | 0 | 0 | 3 | 29 |
| | Total | | | 716 | | | |
| | Accuracy | | | 77.23% | | | |

Figures 8, 9:
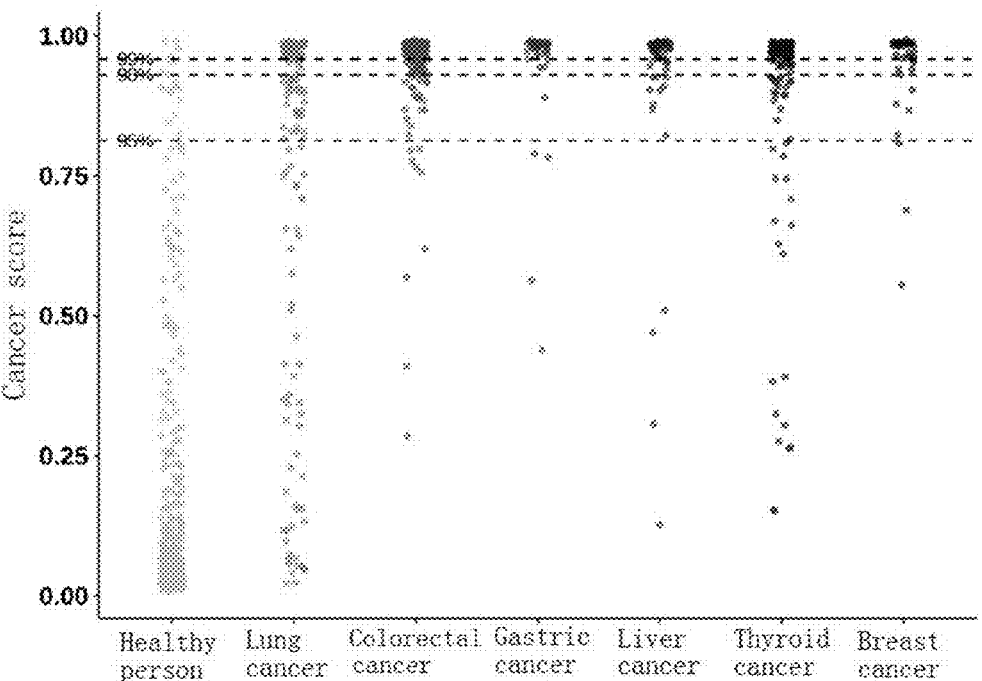
FIG. 8 is a presentation chart of cancer scores on a model training set provided by an embodiment of the present application.
FIG. 9 shows a confusion matrix of a model on a validation set provided by an embodiment of the present application.
Figure 10:
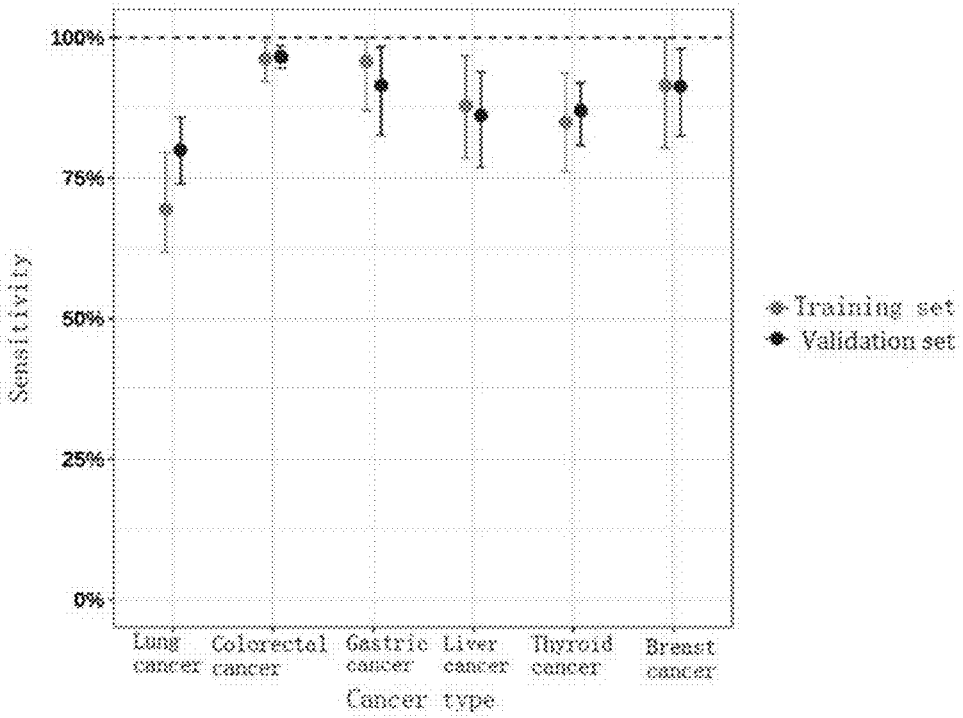
FIG. 10 is a sensitivity chart of a model to different cancers provided by an embodiment of the present application.

By referring to FIG. 8, FIG. 9 and FIG. 10, the embodiments of the present application have excellent accuracy and sensitivity in predicting and tracing the target cancer.

Figure 11:
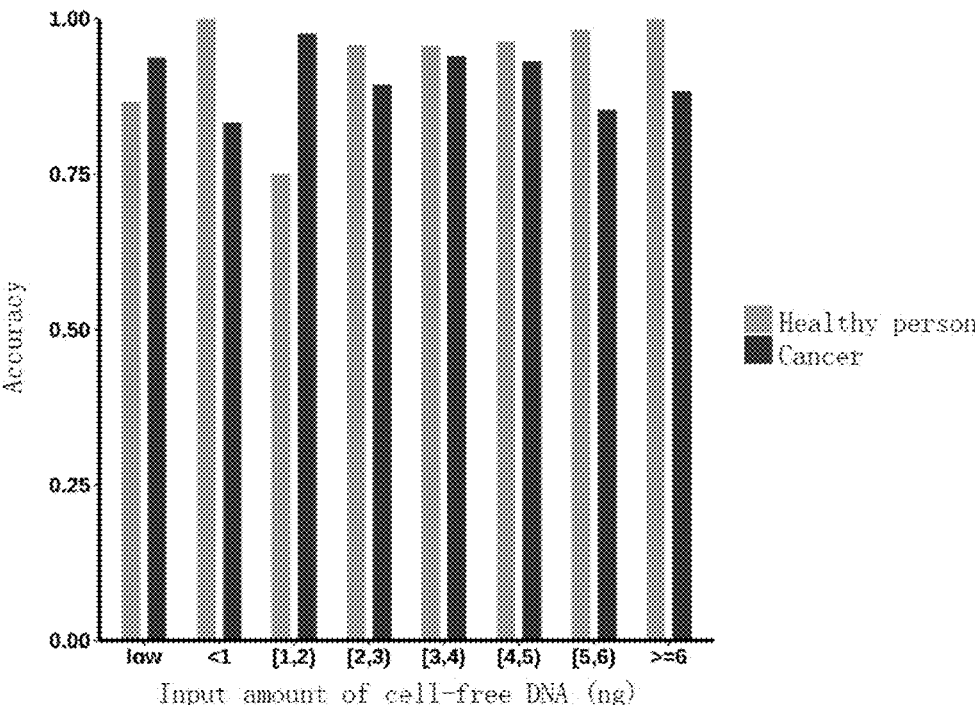
FIG. 11 is an influence chart of an input amount of cell-free DNA on model accuracy provided by an embodiment of the present application.
Figure 12:
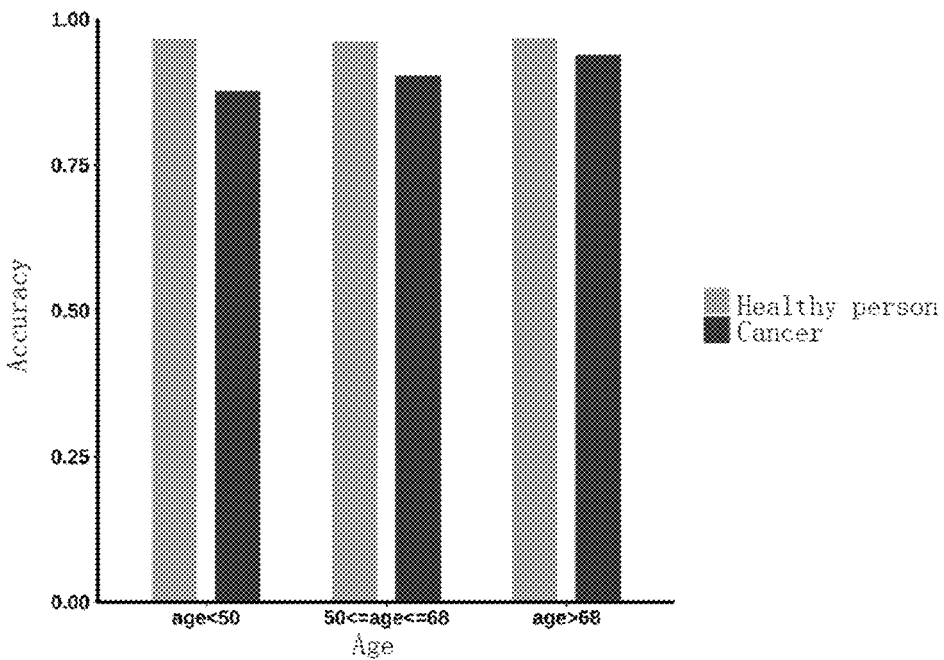
FIG. 12 is an influence chart of ages on the model accuracy provided by an embodiment of the present application.
Figure 13:
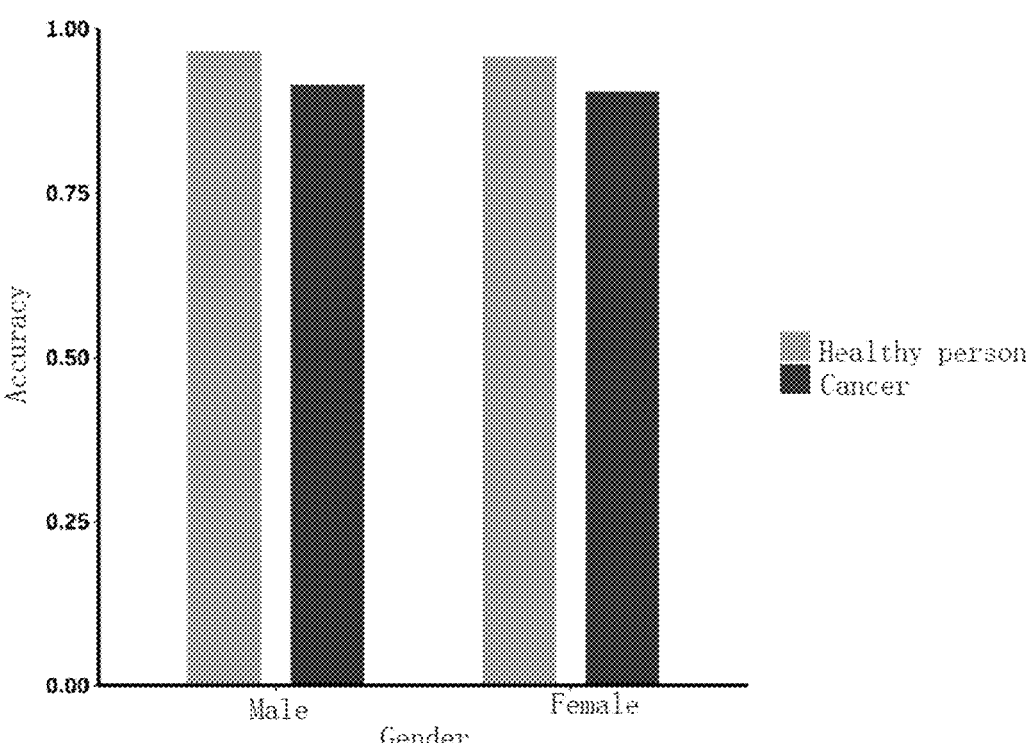
FIG. 13 is an influence chart of genders on the model accuracy provided by an embodiment of the present application.

By referring to FIG. 11, FIG. 12 and FIG. 13, the accuracy of the embodiments of the present application in predicting and tracing the target cancer is less affected by the input amount of cell-free DNA, ages and genders.

The present application has the following beneficial effects:

The present application combines the features related to methylation and fragment omics to train an ensemble machine learning classification model, and has the characteristics of non-invasive detection, low sequencing cost, high detection specificity and sensitivity, etc.

Specific cases are applied herein to illustrate the principle and embodiments of the present application. The above explanation of the embodiments is only used to help to understand the method and the core idea of the present application. Meanwhile, for those ordinary skilled in the art, based on the idea of the present application, the specific embodiments and application scopes may be changed. In conclusion, the content of the description should not be construed as a limitation to the present application.

What is claimed is:

1. A multi-cancer detection system based on high-throughput methylation sequencing of cell-free deoxyribonucleic acid (DNA), comprising:

a first sample sequencing module used for collecting cancer tissue and pericancerous tissue samples of a target cancer, and plasma samples of a target cancer patient and a healthy person, extracting a first genomic DNA of the cancer tissue and pericancerous tissue samples of the target cancer and a first cell-free DNA of the plasma samples of the target cancer patient and the healthy person, and performing methylation sequencing on the first genomic DNA and the first cell-free DNA respectively to obtain sequencing data of the first genomic DNA and sequencing data of the first cell-free DNA;

a first methylation feature set acquisition module used for performing quality control on the sequencing data of the first genomic DNA and the sequencing data of the first cell-free DNA, the quality control comprising at least one of: ensuring a CGG/TGG ratio greater than 0.6, ensuring a mapping rate greater than 0.4, ensuring a number of reads mapped to a human reference genome is greater than 10 million, ensuring a number of CGI islands covering more than 10× is greater than 10,000, and ensuring a number of CpG sites covering more than 10× is greater than 1 million; and mapping the sequencing data of the first genomic DNA and the sequencing data of the first cell-free DNA respectively to the human reference genome to obtain first coordinates of the sequencing data of the first genomic DNA and the sequencing data of the first cell-free DNA on the human reference genome, wherein the first coordinates comprise a beginning position and an end position of each sequence read in the human reference genome; dividing the human reference genome into a plurality of CpG Island regions according to the first coordinates, and counting methylation levels of the sequencing data of the first genomic DNA about different preset haploid algorithms on the plurality of CpG Island regions; comparing differences in the methylation levels of the sequencing data of the first genomic DNA about different haploid algorithms on the plurality of CpG Island regions to obtain cancer-specific regions of the sequencing data of the first genomic DNA about each of the different haploid algorithms; and counting the methylation levels of the sequencing data of the first genomic DNA about the different preset haploid algorithms on the cancer-specific regions to obtain a methylation feature set of the first cell-free DNA;

a first terminal motif feature acquisition module used for taking all base data of p base pairs of 3' terminal of the sequencing data of the first cell-free DNA on the human reference genome as a terminal motif base fragment set, and taking a proportion of each base fragment in the terminal motif base fragment set in a permutation and combination of all base sequences of the p base pairs as a terminal motif feature of the first cell-free DNA;

a first breakpoint motif feature acquisition module used for taking all base data of upstream and downstream q base pairs of the 3' terminal of the sequencing data of the first cell-free DNA on the human reference genome as a breakpoint motif base fragment set, and taking a proportion of each base fragment in the breakpoint motif base fragment set in a permutation and combination of all base sequences of 2*q base pairs as a breakpoint motif feature of the first cell-free DNA; and a detection model building module used for training a learning classification module by taking the methylation feature set of the first cell-free DNA, the terminal motif feature of the first cell-free DNA, and the breakpoint motif feature of the first cell-free DNA as input vectors, and whether cancer is suffered from as an output vector to obtain a trained multi-cancer detection model which is used for detecting whether a target object suffers from the target cancer.

2. The multi-cancer detection system based on high-throughput methylation sequencing of cell-free DNA according to claim 1, wherein the target cancer comprises: lung cancer, gastric cancer, colorectal cancer, liver cancer, breast cancer or thyroid cancer.

3. The multi-cancer detection system based on high-throughput methylation sequencing of cell-free DNA according to claim 1, wherein the different preset haploid algorithms comprise Methylation Mean (MM), Methylation Haplotype Load (MHL), Cell Heterogeneity-Adjusted clonal Methylation (CHALM), Partial Methylation Ratio (PDR) and Entropy.

4. The multi-cancer detection system based on high-throughput methylation sequencing of cell-free DNA according to claim 1, wherein the first sample sequencing module comprises:

a first sample collection unit used for collecting 10 mL of whole blood samples of the target cancer patient and the healthy person respectively by using cell-free DNA blood collection tubes;

a cell-free DNA extraction unit used for extracting the first cell-free DNA from the whole blood samples after plasma separation by using a plasma DNA extraction kit; and a cell-free DNA sequencing unit used for building a library and degenerating representative bisulfite sequencing for the first cell-free DNA to obtain the sequencing data of the first cell-free DNA.

5. The multi-cancer detection system based on high-throughput methylation sequencing of cell-free DNA according to claim 1, wherein the first sample sequencing module further comprises:

a second sample collection unit used for collecting the cancer tissue and pericancerous tissue samples of the target cancer;

a genomic DNA extraction unit used for extracting the first genomic DNA from the cancer tissue and pericancerous tissue samples of the target cancer by using a genomic DNA extraction kit; and a genomic DNA sequencing unit used for building a library and degenerating representative bisulfite sequencing for the first genomic DNA to obtain the sequencing data of the first genomic DNA.

6. The multi-cancer detection system based on high-throughput methylation sequencing of cell-free DNA according to claim 1, wherein the first methylation feature set acquisition module comprises:

a control group setting unit used for taking samples of each cancer in the target cancer as a positive control group respectively, and taking pericancerous samples corresponding to the target cancer as a negative control group; and a control group comparison unit used for comparing P values of the methylation levels of the positive control group and the negative control group about the different haploid algorithms after multiple test and correction to obtain the cancer-specific regions of all target cancer samples.

7. The multi-cancer detection system based on high-throughput methylation sequencing of cell-free DNA according to claim 1, wherein the learning classification module comprises a first sub-module and a second sub-module connected with the first sub-module, and ensemble algorithms are embedded into the first sub-module; the ensemble algorithms comprise: a logistic regression model algorithm, a support vector machine algorithm, a random forest algorithm, a gradient boosting tree algorithm, a Bayesian model algorithm, a K-nearest neighbor algorithm, an XGBoost algorithm and a CatBoost algorithm; the second sub-module is built-in with a logistic regression model; the ensemble algorithms are used for training the methylation feature set of the first cell-free DNA, the terminal motif feature of the first cell-free DNA, and the breakpoint motif feature of the first cell-free DNA; and the logistic regression model is used for integrating and outputting training results of the ensemble algorithms.

8. The multi-cancer detection system based on high-throughput methylation sequencing of cell-free DNA according to claim 1, wherein the p is any integer between 4 and 10, and the q is any integer between 2 and 5.

9. A multi-cancer traceability system based on high-throughput methylation sequencing of cell-free deoxyribonucleic acid (DNA), comprising:

a second sample sequencing module used for collecting cancer tissue and pericancerous tissue samples of a target cancer, and a plasma sample of a target cancer patient, extracting a second genomic DNA of the cancer tissue and pericancerous tissue samples of the target cancer and a second cell-free DNA of the plasma sample of the target cancer patient, and performing methylation sequencing on the second genomic DNA and the second cell-free DNA respectively to obtain sequencing data of the second genomic DNA and sequencing data of the second cell-free DNA;

a second methylation feature set acquisition module used for mapping the sequencing data of the second genomic DNA and the sequencing data of the second cell-free DNA respectively to a human reference genome after quality control is performed on the sequencing data of the second genomic DNA and the sequencing data of the second cell-free DNA to obtain second coordinates of the sequencing data of the second genomic DNA and the sequencing data of the second cell-free DNA on the human reference genome; dividing the human reference genome into a plurality of CpG Island regions according to the second coordinates, and counting methylation levels of the sequencing data of the second genomic DNA about different haploid algorithms on the plurality of CpG Island regions; comparing differences in the methylation levels of the sequencing data of the second genomic DNA about preset haploid algorithms on the plurality of CpG Island regions to obtain tissue-specific regions of the sequencing data of the second genomic DNA about each of the different haploid algorithms; and counting the methylation levels of the sequencing data of the second genomic DNA about the preset haploid algorithms on the tissue-specific regions to obtain a methylation feature set of the second cell-free DNA;

a second terminal motif feature acquisition module used for taking all base data of p base pairs of 3' terminal of the sequencing data of the second cell-free DNA on the human reference genome as a terminal motif base fragment set, and taking a proportion of each base fragment in the terminal motif base fragment set in a permutation and combination of all base sequences of the p base pairs as a terminal motif feature of the second cell-free DNA;

a second breakpoint motif feature acquisition module used for taking all base data of upstream and downstream q base pairs of the 3' terminal of the sequencing data of the second cell-free DNA on the human reference genome as a breakpoint motif base fragment set, and taking a proportion of each base fragment in the breakpoint motif base fragment set in a permutation and combination of all base sequences of 2*q base pairs as a breakpoint motif feature of the second cell-free DNA; and a traceability model building module used for training a learning classification module by taking the methylation feature set of the second cell-free DNA, the terminal motif feature of the second cell-free DNA, and the breakpoint motif feature of the second cell-free DNA as input vectors, and a probability of suffering from a cancer as an output vector to obtain a trained multi-cancer traceability model which is used for judging types of a detected cancer.

* * * * *